United States Patent [19]

Slusarchyk

[11] Patent Number: 5,369,098
[45] Date of Patent: Nov. 29, 1994

[54] HYDROXYMETHYL CYCLOBUTYL PURINES

[75] Inventor: William A. Slusarchyk, Skillman, N.J.

[73] Assignee: E. R. Squibb & Sons, Inc., Princeton, N.J.

[21] Appl. No.: 367,167

[22] Filed: Jun. 16, 1989

Related U.S. Application Data

[63] Continuation-in-part of Ser. No. 220,849, Jul. 18, 1988, abandoned.

[51] Int. Cl.$^5$ .................. A61K 31/675; A61K 31/52; C07D 473/40; C07D 473/36
[52] U.S. Cl. ........................ 514/81; 514/261; 544/264; 544/276; 544/277; 544/314; 544/317; 544/254; 544/265
[58] Field of Search ............... 544/276, 277, 264, 244; 514/261, 81

[56] References Cited

U.S. PATENT DOCUMENTS

| | | | |
|---|---|---|---|
| 4,177,348 | 12/1979 | Shealy et al. | 544/317 |
| 4,232,154 | 11/1980 | Shealy et al. | 544/250 |
| 4,617,304 | 10/1986 | Ashton et al. | 514/261 |
| 4,743,689 | 5/1988 | Shimada et al. | 544/277 |
| 4,782,062 | 11/1988 | Tolman et al. | 514/262 |
| 4,810,710 | 1/1989 | Mac Coss et al. | 544/244 |
| 4,855,466 | 8/1989 | Zahler et al. | 549/546 |
| 4,859,680 | 8/1989 | Ashton et al. | 514/274 |
| 4,918,075 | 4/1990 | Zahler et al. | 514/262 |
| 4,968,674 | 11/1990 | Taniyama et al. | 514/63 |

FOREIGN PATENT DOCUMENTS

| | | |
|---|---|---|
| 182315 | 5/1986 | European Pat. Off. . |
| 2208295 | 9/1987 | Japan . |

OTHER PUBLICATIONS

Kim et al., "Potential Anit-Aids Drugs . . . ", J. Med. Chem., 30, 862–66 (1987).
Aerschot et al., "Synthesis And Anti-HIV Activity . . . " Nucleosides of Nucleotides, 10 (1–3), 589–90 (1991).
Clement et al., "Cyclobutyl Compounds . . . ", Transplantation Proceedings, vol. 23, No. 3 (Suppl.3) pp. 159–161 (1991).
Bisacchi et al., "Synthesis and Antiviral Activity . . . " J. Med. Chem. (1991), 34, pp. 1415–1421.
Katagiri et al. "Synthesis of . . . " Chem. Pharm. Bull. 38 (11) 3184–86 (1990).
N. Shimada, et al., Oxetanocin, A Novel Nucleoside from Bacteria, Nov. 1986, J. Antibiotics 39, p. 1623.
H. Nakamura, et al., The X-Ray Structure Determination of Oxetanocin, Nov. 1986, J. Antibiotics, 39, p. 1626.
H. Hoshino, et al., Inhibition of Infectivity of Human Immunodeficiency Virus By Oxetanocin, Jul. 1987, J. Antibiotics, 40. p. 1077.
S. Niitsuma et al., Studies on the Total Synthesis of Oxetanocin; The First Synthesis of a Nucleside Having Oxetanosyl-N-Glycoside[1]. Tetrahedron Letters, vol. 28, pp. 3967–3970, May 1987.
S. Niitsuma et al., Studies on the Total Synthesis of Oxetanocin; Tetrahedron Letters, vol. 28, pp. 4713–4714, May 1987.
G. N. Austin et al., Chiral Oxetanes from Sugar Lactones, Tetrahedron Letters, vol. 28, pp. 4741–4744, May 1987.
N. Shimada-Derivatives of Oxetanocin: Oxetanocins H. X and G. and 2-Aminooxetanocin A, J. Antibiotics, vol. 40, p. 1789, Dec. 1987.
M. Hanack, et al.–Solvolysen von Δ$^2$-Cyclobutenylmethyl-tosylate[2]), Chem. Ber. 100, p. 2107 1967.
Marques, et al., Medicinal Research Reviews, vol. 6, No. 1, John Wiley & Sons, Inc. pp. 1–16 and 36–40 1969.
De Clercq, et al., Nucleosides and Nucleotides, vol. 8(5 & 6), pp. 659–671 (1989).
Vince, et al., J. Med. Chem., vol. 33(1), pp. 17–21 (Jan. 1990).

Primary Examiner—Mukund J. Shah
Assistant Examiner—Matthew Y. Grumbling
Attorney, Agent, or Firm—Stephen B. Davis

[57] ABSTRACT

Antiviral activity is exhibited by compounds having the formula
(Abstract continued on next page.)

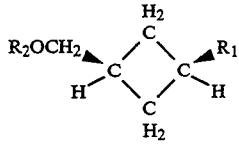
and their pharmaceutically acceptable salts.
R$_1$ is
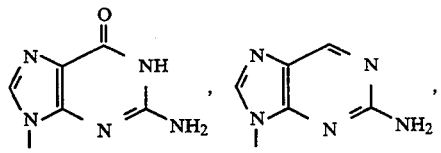
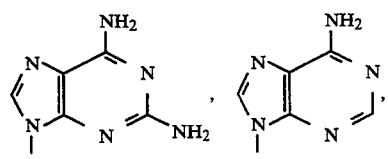
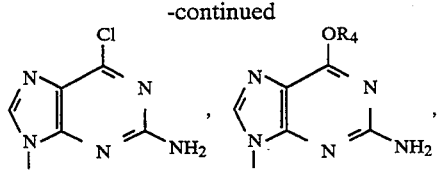
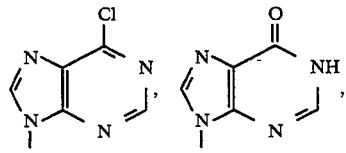
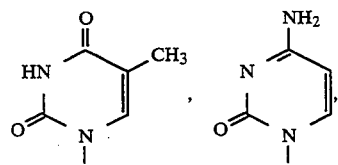
R$_2$ is hydrogen, —PO$_3$H$_2$,
or $-\overset{\overset{O}{\|}}{C}-R_3$
wherein R$_3$ is hydrogen, alkyl, substituted alkyl, or aryl, and R$_4$ is alkyl.
12 Claims, No Drawings

HYDROXYMETHYL CYCLOBUTYL PURINES

BRIEF DESCRIPTION OF THE INVENTION

This application is a continuation-in-part of co-pending application Ser. No. 220,849 filed Jul. 18, 1988, now abandoned.

Antiviral activity is exhibited by compounds having the formula

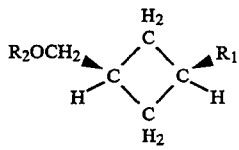

and its pharmaceutically acceptable salts. In formula I, and throughout the specification, the symbols are as defined below.

$R_1$ is

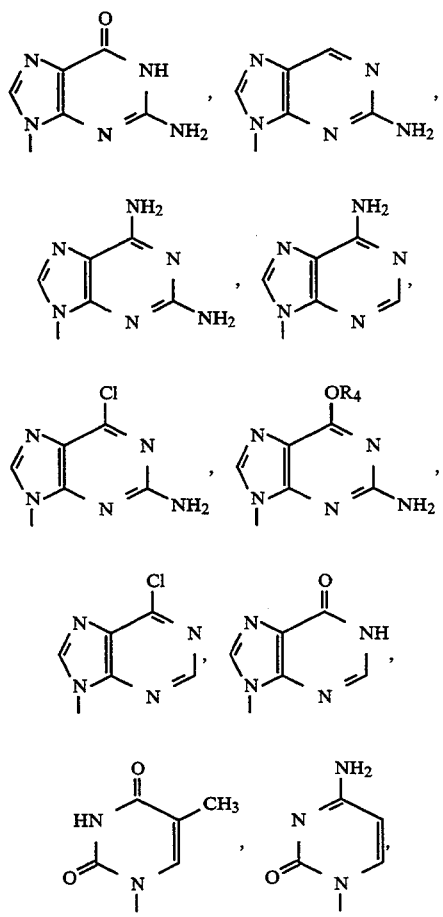

$R_2$ is hydrogen, —$PO_3H_2$,

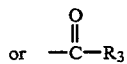

wherein $R_3$ is hydrogen, alkyl, substituted alkyl, or aryl and $R_4$ is alkyl.

Preferred compounds of formula 1 are when $R_1$ is

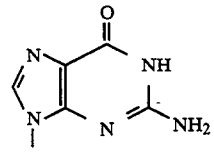

and

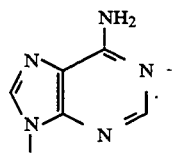

The term "alkyl" refers to both straight and branched chain groups. Those groups having 1 to 10 carbons are preferred. The term "substituted alkyl" refers to alkyl groups having one or more substituents. Preferred substituents are halogen, amino, axido, hydroxy, cyano, triakylammonium (wherein each alkyl group has 1 to 6 carbons), alkoxy of 1 to 6 carbons, aryl and carboxy. The term "aryl" as used here, refers to phenyl and phenyl substituted with one, two or three substituents. Preferred substituents are alkyl of 1 to 6 carbons, alkoxy of 1 to 6 carbons, halogen, trifluoromethyl, amino, alkylamino, dialkylamino, nitro, cyano, alkanoyloxy of 2 to 11 carbons, carboxy, carbamoyl and hydroxy.

DETAILED DESCRIPTION OF THE INVENTION

The compounds of formula 1, and the pharmaceutically acceptable salts thereof, are antiviral agents that can be used to treat viral infection in mammalian species such as domesticated animals (e.g., dogs, cats, horses and the like) and humans, and avian species (e.g., chickens and turkeys). The compounds of formula 1 wherein $R_1$ is

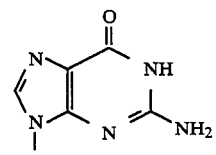

and

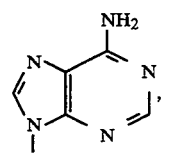

are effective against one or more of the following viruses: herpes simplex virus 1 and 2, varicellazoster virus, murine leukemia virus and human immunodeficiency virus (HIV). They are also believed to be active against a variety of other DNA and retroviruses. Exemplary DNA viruses in addition to those named above include other herpes viruses (e.g., Epstein-Barr virus, pseudorabies virus, other poxviruses (e.g. monkey pox and myoma), papovaviruses (e.g., the papilloma viruses), hepatitis B virus, and adenoviruses. Exemplary retroviruses in addition to those named above include those effecting man, such as human T-cell lymphotropic viruses (HTLV), and those effecting other animals, such as feline leukemia virus and equine infectious anemia virus. All of the other compounds of formula 1 are believed to be active against one or more of the following viruses: herpes simplex virus 1 and 2, varicella-zoster virus, cytomegalovirus, murine leukemia virus, human immunodeficiency virus and the other viruses described above.

The compounds of this invention may be administered parenterally (for example, by intravenous, intraperitoneal or intramuscular injection), orally or topically.

The compounds may be administered orally or parenterally in an amount effective to treat the infection. The dosage will, of course, depend on the severity of the infection, but will likely be in the range of about 1.0 to 50 mg/kg of body weight. The desired dose may be administered several times daily at appropriate intervals.

For infections of the eye, or other external tissues, e.g. mouth and skin, the compositions may be applied to the infected part of the body of the patient topically as an ointment, cream, aerosol, gel, powder, lotion, suspension or solution (e.g. as in eye drops). The concentration of the compound in the vehicle will, of course, depend on the severity of the infection, but will likely be in the range of about 0.1 to 7% by weight.

A compound of formula 1 wherein $R_1$ is

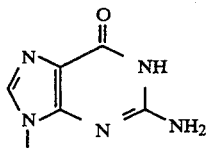

and $R_2$ is hydrogen can be prepared from an intermediate of formula

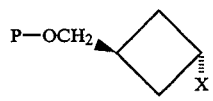

2 wherein P is a protecting group such as acyl, or silyl, and X is a leaving group such as chloro, bromo, iodo or an aryl or alkyl sulfonate (e.g., p-toluenesulfonyloxy or methanesulfonyloxy).

The term "acyl" refers to groups

wherein $R_5$ is a lower alkyl group of 1–6 branched or straight chain carbon atoms or a phenyl group. The term "silyl" refers to silyl protecting groups well known in the art [e.g., t-butyldimethylsilyl, t-butyl diphenylsilyl, (triphenylmethyl) dimethylsilyl, methyldiisopropylsilyl, or triisopropylsilyl].

Reaction of a compound of formula 2 with a protected form of guanine such as a compound of formula

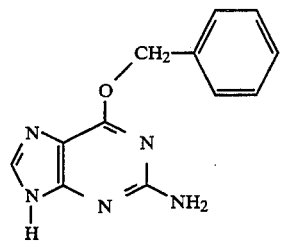

3 in the presence of a base such as potassium carbonate, sodium hydride, or potassium hydride in an aprotic polar solvent such as dimethylformamide, dimethyl sulfoxide, or sulfolane (tetramethylene sulfone) yields the corresponding compound of formula

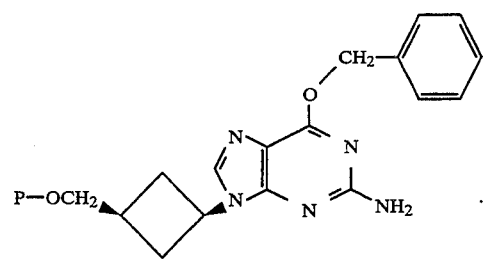

4

Optionally, the reaction can be run in the presence of a metal chelating agent such as 18-crown-6 (1,4,7,10,13,16-hexaoxacyclooctadecane) or 15-crown-5 (1,4,7,10,13-pentaoxacyclopentadecane). Removal of the protecting groups from a compound of formula 4 yields a compound of formula 1 wherein $R_1$ is

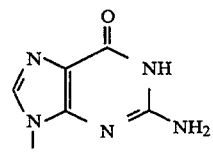

and $R_2$ is hydrogen.

When the protecting group P in 4 is an acyl group, the protecting group P can be selectively removed using, for example, catalytic sodium methoxide in methanol or methanolic ammonia. Subsequent removal of the O-benzyl protecting group on the purine moiety can be accomplished by treatment with aqueous alcoholic mineral acid (e.g., aqueous methanolic hydrochloric acid), sodium in liquid ammonia, or by hydrogenolysis e.g., palladium hydroxide on carbon in cyclohexene and ethanol). Alternatively, the purine O-benzyl protecting group can be removed initially, followed by removal of the acyl protecting group.

When the group P in compound 4 is a silyl protecting group, removal of the P group can be accomplished using fluoride ion (e.g., tetrabutylammonium fluoride in tetrahydrofuran). The purine O-benzyl protecting group can then be removed with aqueous alcoholic mineral acid, sodium in liquid ammonia, or by hydrogenolysis.

The preparation of a compound of formula 2 is outlined in the following schematic:

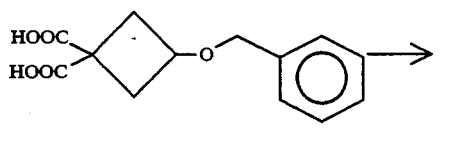

5

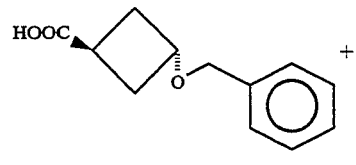

6

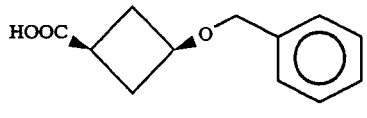

7

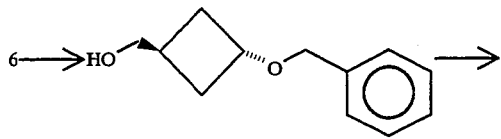

8

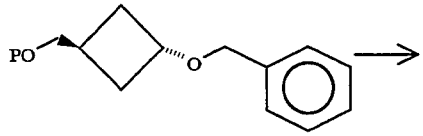

9

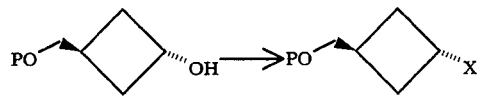

10   2

A compound of formula 2 can be synthesized from a compound of formula 5, whose preparation is described in the literature (See C. J. Michejda et al., J. Org. Chem., 40, 1046 (1975) and C. Beard et al., Chem. Ber., 95, 2535 (1962)). Heating a compound of formula 5 in vacuo according to the literature (C. Beard et al., Chem., Ber., 95, 2535 (1962); J. Safanda et al., Coll. Czech. Chem. Communs., 47, 2441 (1982)) affords a compound of formula 6, having a m.p. 46°–48°, and a more polar compound of formula 7 as an oil. (Note: C. Beard et al. and J. Safanda et al. incorrectly designated the crystalline product as having structure 7 and the more polar oily product as having structure 6). Treatment of the crystalline compound of formula 6 with a reducing agent such as lithium aluminum hydride in a solvent such as diethyl ether or tetrahydrofuran yields alcohol 8. The hydroxyl group can be protected as an acyl ester or a silyl ether by methods known in the art, yielding a compound of formula 9. Reduction of the benzyl group in 9 using for example, palladium hydroxide on carbon, ethanol and cyclohexene, provides a compound of formula 10. The compound of formula 10 can be converted to a compound of formula 2 by methods known in the art. For example, treatment of 10 with p-toluenesulfonyl chloride or methanesulfonyl chloride in pyridine yields a compound of formula 2 wherein X is p-toluenesulfonyloxy or methanesulfonyloxy, respectively. The compound of formula 2 wherein P is benzoyl and X is p-toluenesulfonyloxy has a melting point 81°–82°, and its structure was confirmed by a single crystal X-ray analysis. The compound of formula 2 wherein X is p-toluenesulfonyloxy or methanesulfonyloxy can also be prepared from a compound of formula 13 by treatment with p-toluenesulfonic acid or methanesulfonic acid, respectively, in the presence of triethylamine, triphenylphosphine, and diethyl or diisopropyl azodicarboxylate in a solvent such a toluene, ether or dioxane.

The compound of formula 13 can be prepared from a compound of formula 7 following the methodology used to convert compound 6 to the compound of formula 10. Treatment of 7 with lithium aluminum hydride affords a compound of formula 11. Protection of the hydroxyl group in 11 yields a compound of formula 12 and debenzylation gives the compound of formula 13.

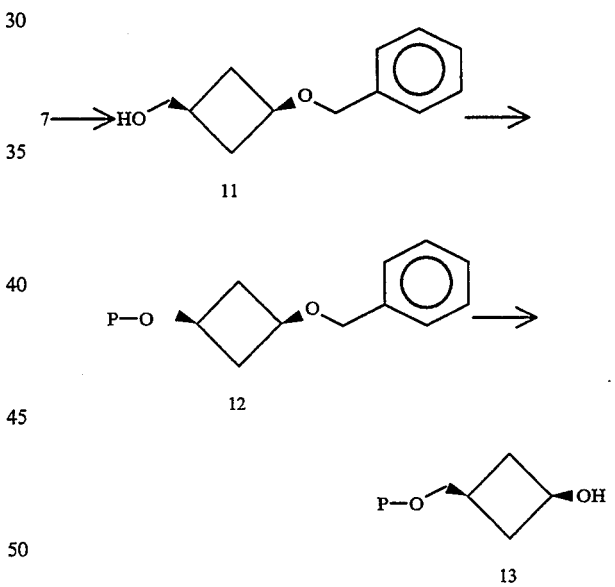

11

12

13

Alternatively, treatment of the compound of formula 13 with a methyltriphenoxyphosphonium halide or methyltriphenylphosphonium halide (i.e., chloride, bromide or iodide) in a solvent such as dimethylformamide provides a compound of formula 2 wherein X is chloro, bromo, iodo. In yet another alternative, a compound of formula 2 wherein X is chloro, bromo, or iodo can be prepared from the compound of formula 13 using triphenylphosphine, diethyl (or diisopropyl) azodicarboxylate, and a source of halide such as methyl iodide, methyl bromide, or dichloromethane according to methodology known in the art. See, for example, H. Loibner et al. Helv. Chim. Acta. 59, 2100 (1976).

Reaction of a compound of formula 2 with compound

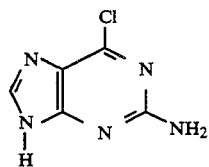

14 under conditions analogous to those used in the preparation of compound 4 provides a compound of formula

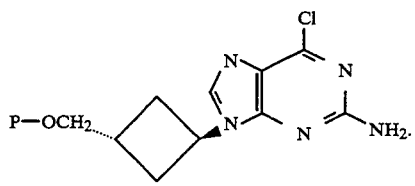

15

Selective removal of the protecting group P provides a compound of formula 1 wherein $R_1$ is

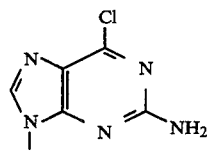

and $R_2$ is hydrogen. For example, when the protecting group P in 15 is acyl, the P group can be selectively removed using, for example, catalytic sodium methoxide in methanol. When the protecting group P in 15 is silyl, the protecting group can be selectively removed by treatment with fluoride ion (e.g., tetrabutylammonium fluoride).

Acid hydrolysis (e.g., using hot aqueous hydrochloric acid) of the chloro group of a compound of formula 1 wherein $R_1$ is

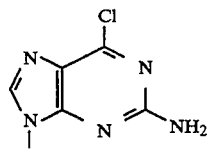

and $R_2$ is hydrogen provides a compound of formula 1 wherein $R_1$ is

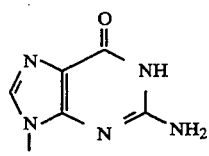

and $R_2$ is hydrogen.

A compound of formula 1 wherein $R_1$ is

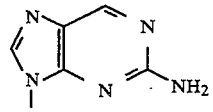

and $R_2$ is hydrogen can be prepared from a compound of formula 15. For example, when the P group in 15 is an acyl or silyl protecting group, the chloro group can first be reduced by hydrogenation (e.g. ammonium formate and palladium on carbon in methanol or ethanol; palladium on carbon and cyclohexene in ethanol; or palladium on carbon, hydrogen and ethanol) and then the protecting group P can be removed using either catalytic sodium methoxide in methanol or methanolic ammonia when P is acyl, and fluoride ion when P is silyl. Alternatively, the acyl or silyl protecting group P can be removed first and then the chloro group can be reduced.

Alternatively, this compound of formula 1 can be prepared by reacting an optionally protected compound of formula

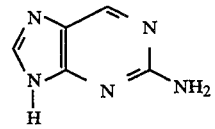

16 with a compound of formula 2 according to procedures analogous to those used in the preparation of a compound of formula 4, followed by removal of the protecting groups by methods known in the art. An optionally protected form of compound 16 can be protected at the amino (—NH$_2$) group by such exemplary groups as acyl, trityl, or substituted trityl. Exemplary substituted trityl groups are 4-monomethoxytrityl and 4,4'-dimethoxytrityl.

A compound of formula 1 wherein $R_1$ is

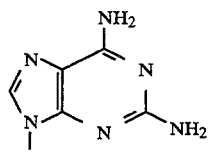

and $R_2$ is hydrogen can be prepared from a compound of formula 15 by treatment with hot methanolic ammonia according to methods known in the art (e.g., J. C. Martin, et al., J. Med. Chem. 28, 358(1985)). When the protecting group P in 15 is acyl, for example, treatment with hot methanolic ammonia results in substitution of the chloro group by an amino group and simultaneous removal of the acyl protecting group. When the protecting group P is a silyl group, replacement of the chloro group by an amino group can be accomplished first, and then the protecting group P can be removed, for example, by treatment with fluoride ion.

Alternatively, the compound of formula 1 can be prepared by reacting a an optionally protected compound of formula

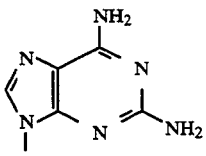

17 with a compound of formula 2 according to procedures analogous to those used in the preparation of a compound of formula 4, followed by removal of the protecting group P by methods known in the art. An optionally protected form of 17 can be protected at the amino (—NH$_2$) group by such exemplary groups as acyl, trityl or substituted trityl.

A compound of formula 1 wherein R$_1$ is

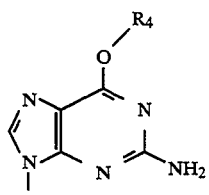

and R$_2$ is hydrogen can be prepared from a a compound of formula 1 wherein R$_1$ is

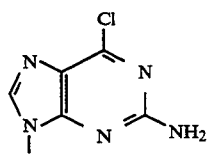

and R$_2$ is hydrogen by methods known in the art. See, for example, J. F. Gerster, et al., J. Amer. Chem. Soc., 87, 3752 (1965); K. K. Ogilvie, et al., Can. J. Chem., 62, 2702 (1984); M. R. Harnden, et al., J. Med. Chem., 30, 1636 (1987).

Alternatively, the compound of formula 1 can be prepared by reacting a compound of formula

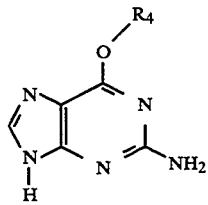

18 with a compound of formula 2 according to procedures analogous to those used in the preparation of a compound of formula 4, followed by removal of the protecting group P by methods known in the art. The compound of formula 18 can be prepared from the compound of formula 14 by methods known in the art. See, for example, W. A. Bowles, et al., J. Med. Chem., 6, 471 (1963); M. MacCoss, et al., Tetrahedron Lett., 26, 1815 (1985).

Reaction of the compound of formula 2 with a compound of formula

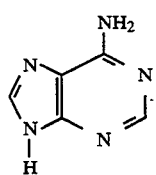

19 by methodology analogous to that used to prepare a compound of formula 4, and subsequent removal of the P protecting group, yields the corresponding compound of formula 1 wherein R$_1$ is

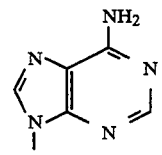

and R$_2$ is hydrogen.

Alternatively, this compound of formula 1 can be prepared by reaction of a compound of formula

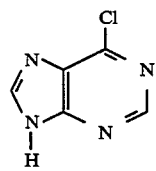

20 with a compound of formula 2 by methods analogous to those used in the preparation of a compound of formula 4. This affords the corresponding compound of formula

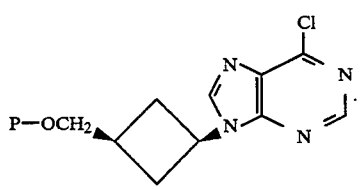

21

Treatment of a compound of formula 21 with hot ammonia in an alcohol (such as, methanol or ethanol) and simultaneous or subsequent deprotection of the P protecting group yields the corresponding compound of formula 1 wherein R$_1$ is

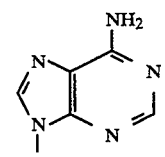

and R$_2$ is hydrogen.

The compound of formula 1 wherein R$_1$ is

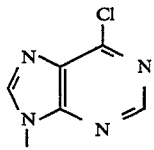

and R$_2$ is hydrogen can be prepared from a compound of formula 21 by selective removal of the P protecting group. For example, when the protecting group P in 21 is acyl, the P group can be selectively removed using, for example, catalytic sodium methoxide in methanol. When the protecting group P in 1 is silyl, the protecting group P can be selectively removed by treatment with fluoride ion e.g., tetrabutylammonium fluoride).

Acid hydrolysis (e.g., using hot aqueous hydrochloric acid) or basic hydrolysis (e.g., aqueous methanolic sodium hydroxide) of the chloro group of a compound of formula 1 wherein R$_1$ is

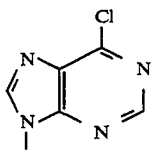

and R$_2$ is hydrogen provides a compound of formula 1 wherein R$_1$ is

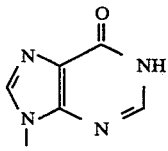

and R$_2$ is hydrogen. Alternatively, this compound of formula 1 can be prepared by treatment of a compound of formula 1 wherein R$_1$ is

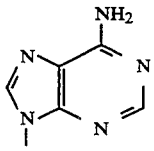

and R$_2$ is hydrogen with adenosine deaminase according to methods known in the art (e.g., M. J. Robins, et al., J. Med. Chem., 27, 1486 (1984); K. K. Ogilvie, et al., Can. J. Chem., 62, 241 (1984)).

The compound of formula 1 wherein R$_1$ is

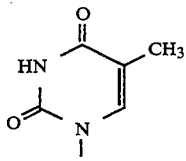

and R$_2$ is hydrogen can be prepared by reaction of a compound of formula 2 with a compound of formula

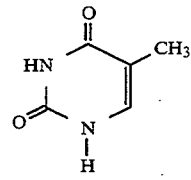

by methodology analogous to that used to prepare a compound of formula 4, and subsequent removal of the P protecting group. For example, when P is acyl, the protecting group can be removed by treatment with sodium methoxide in methanol or methanolic ammonia, or when P is a silyl group, deprotection can be accomplished with fluoride ion.

The compound of formula 1 wherein R$_1$ is

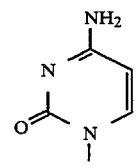

and R$_2$ is hydrogen can be prepared by reaction of a compound of formula 2 with a compound of formula

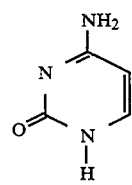

by methodology analogous to that used to prepare a compound of formula 4, and subsequent removal of the P protecting group. Optionally, the amino (—NH$_2$) group in 23 can be protected, e.g., with an acyl group. Removal of this protecting group can be accomplished using sodium methoxide in methanol or methanolic ammonia.

Alternatively, the compound of formula 1 wherein R$_1$ is

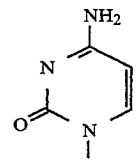

and R$_2$ is hydrogen can be prepared from a compound of formula

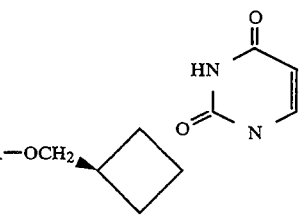

(wherein P is an acyl protecting group) by methods known in the art, and subsequent removal of the P protecting group. See, for example, I. Wempner, et al., in "Synthetic Procedures in Nucleic Acid Chemistry", Vol. 1, W. W. Zorbach and R. S. Tipson, Eds., Interscience Publishers, N.Y., p. 299, 1968; T. S. Lin, et al., J. med. Chem., 26, 1691 (1983); P. Herdewijn, et al., J. Med. Chem., 28, 550 (1985).

The compound of formula 24 can be prepared by reaction of a compound of formula

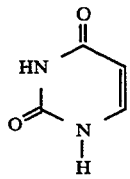

with a compound of formula 2 according to procedures analogous to those used in the preparation of a compound of formula 4.

Compounds of formula 1 wherein $R_2$ is

can be prepared from the corresponding compounds of formula 1 wherein $R_2$ is hydrogen by methods known in the art.

For examples of acylation procedures see: "Synthetic Procedures in Nucleic Acid Chemistry", Vol. 1, W. W. Zorbach and R. S. Tipson, Eds., John Wiley and Sons, 1968; "Nucleic Acid Chemistry," Part 1, L. B. Townsend and R. S. Tipson, Eds., John Wiley and Sons, 1978; S. Nishino, et al., Nucleosides and Nucleotides, 5, 159 (1986); J. C. Martin, et al., J. Pharm. Sci., 76, 180 (1987); A. Matsuda, et al., Synthesis, 385 (1986); J. Zemlicka, et al., Collect. Czech. Chem. Commun., 32, 3159 (1967).

Compounds of the formula 1 wherein $R_2$ is $-PO_3H_2$ can be prepared from the corresponding compounds of formula 1 wherein $R_2$ is hydrogen by procedures known in the art. See, for example, H. Schaller, et al., J. Amer. Chem. Soc., 85, 3821 (1963); J. Beres, et al., J. Med. Chem., 29, 494 (1986); Y. Hayakawa, et al., Tetrahedron Letters, 28, 2259 (1987); F. Himmelsbach, et al., Helv. Chim. Acta., 70, 1286 (1987); "Nucleic Acid Chemistry", Part 2, L. B. Townsend and R. S. Tipson, Eds., John Wiley and Sons, 1978.

The compounds of formula 1 wherein $R_1$ is

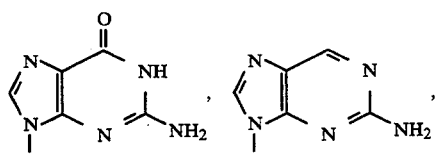

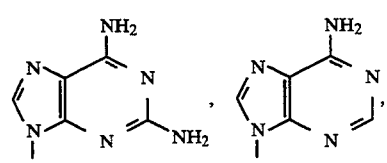

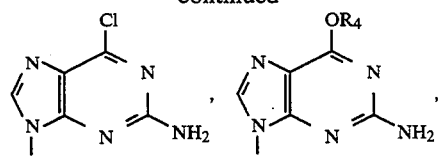

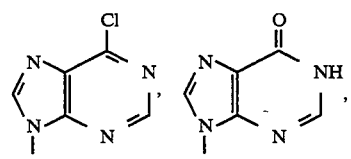

and

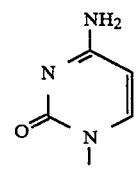

can form basic salts with inorganic or organic acids. Illustrative are the hydrohalide (e.g., hydrochloride and hydrobromide), alkylsulfonate, sulfate, phosphate and carboxylate salts. The compounds of formula 1 wherein $R_1$ is

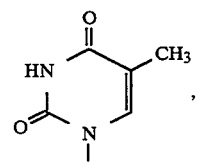

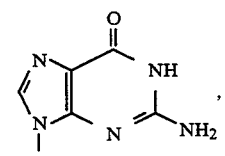

and

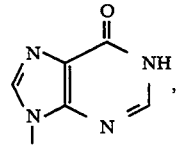

can form basic salts with inorganic and organic bases. Illustrative are alkali metal salts (e.g., sodium and potassium), alkaline earth metal salts (e.g. calcium and magnesium), ammonium and substituted ammonium salts.

The compounds of formula 1 wherein $R_2$ is $-PO_3H_2$ can form basic salts with inorganic and organic bases. Illustrative are the alkali metal salts (e.g., sodium and potassium), alkaline earth metal salts (e.g., calcium and magnesium), ammonium and substituted ammonium salts.

The following examples are specific embodiments of this invention.

EXAMPLE 1

(cis)-2-Amino-1,9-dihydro-9 [3-( hydroxymethyl)cyclobutyl]-6H-purine-6-one

A. 1-Chloro-2-benzyloxy-3-bromopropane

A mixture of benzyl bromide (127 g, 0.74 mol), epichlorohydrin (69 g, 0.74 mol) and 63 mg of mercuric chloride was stirred under nitrogen at 150° for 16 hours. Distillation of the reaction mixture gave 118 g of the desired product as an oil having b.p. 104°/0.5 mm.

B. 3-(Phenylmethoxy)-1,1-cyclobutanedicarboxylic acid, diethyl ester

To a stirred suspension of oil-free sodium hydride (10.7 g, 0.446 mol) in 270 ml of dry dioxane under nitrogen at room temperature was added over twenty minutes 69.1 g (0.432 mol) of diethyl malonate. After the addition, 1-chloro-2-benzyloxy-3-bromopropane (115 g, 0.437 mol) was added over 20 minutes, and the reaction was refluxed for 44 hours. The reaction was cooled to room temperature, and then a slurry of 10.7 g (0.446 mol) of oil-free sodium hydride in 100 ml of dioxane was cautiously added in portions. The mixture was refluxed for 120 hours and cooled to room temperature. The inorganics were removed by filtration, and the filtrate was concentrated in vacuo to an oil, which was partitioned between ether and water. The ether layer was dried ($Na_2SO_4$) and concentrated to an oil, which was distilled to give 58.8 g of desired product having a b.p. 142°-146°/0.3 mm.

C. 3-(Phenylmethoxy)-1,1l-cyclobutanedicarboxylic acid

A mixture of 88 g (0.286 mol) of 3-(phenylmethoxy)-1,1-cyclobutanedicarboxylic acid, diethyl ester in a solution of 72.6 g (1.30 mol) of potassium hydroxide, 183 ml of 95% ethanol and 42 ml of water was refluxed under nitrogen for 2 hours. The reaction mixture was cooled to room temperature and concentrated to a residue, which was taken up in water. After two extractions with ether, the aqueous layer was cooled to 5° and acidified with 25 ml of 6N hydrochloric acid, yielding a brown oil which crystallized upon warming to room temperature. The crystals were collected by filtration and recrystallized from 125 ml of hot water to give 49.8 g of desired product with a m.p. 159°-161° C.

D. (trans)-3-(Phenylmethoxy)cyclobutanecarboxylic acid and (cis)-3-(Phenylmethoxy)cyclobutanecarboxylic acid 3-(Phenylmethoxy)-1,1-cyclobutanecarboxylic acid (42.4 g, 0.169 mol) was heated in vacuo with stirring at 175° and 11 mm for 1 hour and distilled to give 29.2 g of a mixture of (trans) and (cis)-3-(phenylmethoxy)cyclobutanecarboxylic acid as a colorless oil with b.p. 146°-150°/0.4 mm. Chromatography of this oil over 750 g of Whatman LPS-1 silica gel using pentane-ethyl acetate-acetic acid (79:20:1) provided 5.5 g of the crystalline trans isomer and 22 g of a mixture of cis and trans isomers. Chromatography of the 22 g over 750 g of LPS-1 silica gel using the same solvent system afforded additional trans isomer (5.1 g) and 17 g of a mixture of cis and trans isomer. A similar chromatography of the 17 g mixture gave 3 g of the trans isomer and 14 g of (cis)-3-phenylmethoxy)-cyclobutanecarboxylic acid as an oil, containing ca. 10% of the trans isomer. The combined fractions of trans isomer were recrystallized from pentane-diisopropyl ether to give 13 g of crystals (m.p. 46°-48°) consisting of 95% (trans)-3-(phenylmethoxy)-cyclobutanecarboxylic acid and 5% (cis)-3-(phenylmethoxy)cyclobutanecarboxylic acid. Trans isomer: $^1$HNMR ($CDCl_3$, 400 MHz) $\delta$7.2-7.4 (m, 5H), 4.41 (s, 2H), 4.30 (quintet, 1H), 3.07 (m, 1H), 2.53 (m, 2H), 2.34 (m, 2H). Cis isomer: $^1$HNMR ($CDCl_3$, 400 MHz) $\delta$7.2-7.4 (m, 5H), 4.43 (s, 2H), 3.96 (septet, 1H), 2.64 (m, 1H), 2.50 (m, 2H), 2.29 (m, 2H).

E. (trans)-3-Phenylmethoxy)cyclobutanemethanol

To a stirred suspension of 1.14 g (30 mmol) of lithium aluminum hydride in 120 ml of ether under nitrogen at 0°-5° was added, dropwise over 20 minutes, 4.12 g (20 mmol) of (3-phenylmethoxy)cyclobutanecarboxylic acid (95% trans+5% cis) in 60 ml of ether. The cooling bath was removed, and the mixture was stirred at room temperature for 1 hour. Wet ether was added dropwise to the mixture cooled in an ice-water bath. The pH was adjusted to 1.5 using 6N HCl and the phases were separated. The aqueous layer was extracted twice with ether, and the combined ether extracts were dried ($Na_2SO_4$) and evaporated in vacuo to give 3.9 g of desired product as an oil.

F. (trans)-3-(Phenylmethoxy)cyclobutanemethanol, benzoate ester

Benzoyl chloride (2.37 ml, 20.5 mmol) was added dropwise to a stirred solution of the above preparation of (trans)-3-(phenylmethoxy)cyclobutanemethanol (3.9 g) in 35 ml of dry pyridine under nitrogen cooled in an ice-water bath. The bath was removed, and the mixture was stirred for 2 hours at room temperature. Water (17 ml) was added, and the reaction was stirred overnight. The solvents were removed in vacuo, and the residue was taken up in ethyl acetate and water. The ethyl acetate layer was washed sequentially with 1N HCl, water, saturated aqueous $NaHCO_3$, and water, and then dried ($Na_2SO_4$) and concentrated in vacuo to give 5.7 g of desired product as an oil.

G. (trans)-3-Hydroxycyclobutanemethanol, benzoate ester

A stirred mixture of 3.6 g of the above preparation of (trans)-3-(phenylmethoxy)cyclobutanemethanol, benzoate ester, 2.52 g of 20% palladium hydroxide on carbon, 144 ml of absolute ethanol, and 44 ml of cyclohexene was refluxed under nitrogen for 15 minutes. The reaction mixture was cooled to room temperature and filtered through Celite. Concentration of the filtrate in vacuo gave 2.6 g of desired product as an oil.

H. (trans)-3-[[(4-Methylphenyl)sulfonyl]oxy]-cyclobutanemethanol, benzoate ester p-Toluenesulfonyl chloride (3.47 g, 18.2 mmol) was added to a solution of the above preparation of (trans)-3-hydroxycyclobutanemethanol, benzoate ester (2.5 g) in dry pyridine (35 ml) under nitrogen, and the mixture was stirred at 60° for 18 hours. Water (20 ml) was added, and heating was continued for 4 hours longer. The reaction was cooled to room temperature and concentrated in vacuo to a solid, which was dissolved in ethyl acetate and water. The ethyl acetate layer was washed with water, saturated aqueous $NaHCO_3$, and water, dried ($Na_2SO_4$), and concentrated to a solid (3.8 g). This solid was combined with 1.5 g of solid from a similar preparation. Chromatography of these solids over 200 g of LP-1 silica gel, using hexane-ethyl acetate (6:1), gave (trans)-3-[[(4-methylphenyl)sulfonyl]oxy]cyclobutanemethanol, benzoate ester containing varying amounts of its cis-isomer as shown below:

| Column Fraction | Amount (g) | % trans |
|---|---|---|
| 1 | 0.25 | 100 |
| 2 | 0.38 | >95 |
| 3 | 1.9 | 95 |
| 4 | 1.9 | 80 |

I. (cis)-3-[2-Amino-6-(phenylmethoxy)-9H-purin-9yl]cyclobutanemethanol benzoate ester A mixture of 3-[[(4-methylphenyl)sulfonyl]-oxy]cyclobutanemethanol, benzoate ester (95% trans +5% cis, 720 mg 2 mmol), 2-amino-6-(phenylmethoxy)- 9H-purine (724 mg, 3 mmol), 18-crown-6 (528 mg, 2 mmol), and potassium carbonate (414 mg, 3 mmol) in 20 ml of dry dimethylformamide under nitrogen was stirred at 110° for 18 hours. The reaction mixture was concentrated in vacuo to an oil, absorbed onto Baker silica gel using dichloromethane and chromatographed over 200 ml of LPS-1 silica gel, using ethyl acetate-hexane (7:3), to give 447 mg of desired product as a residue.

J. (cis)-3-[2-Amino-6-(phenylmethoxy)-9H-purin-9-yl]cyclobutanemethanol

To 440 mg (1.03 mmol) of (cis)-3-[2-amino6-(phenylmethoxy)-9H-purin-9-yl]cyclobutanemethanol, benzoate ester in 15 ml of dry methanol under nitrogen was added 68 μl of 25% sodium methoxide in methanol. The mixture was stirred at 40° for 2 hours and then concentrated to a residue. The residue was suspended in water, and the pH was adjusted to 7.0 using 1N HCl. Removal of water in vacuo gave a residue, which was triturated with hexane. Evaporation of the hexane afforded 330 mg of crude desired product as a foam.

K. (cis)-2-Amino-1,9-dihydro-9-[3-hydroxymethyl)-cyclobutyl]-6H-purine-6-one

To a solution of the above preparation of (cis)-3-[2-amino-6-(phenylmethoxy)-9H-purin-9-yl]-cyclobutanemethanol (330 mg) in 5.2 ml of methanol was added 2.6 ml of 3N HCl. The mixture was stirred under nitrogen at 40° for 2 hours and concentrated in vacuo to a solid, which was suspended in water. The pH was adjusted to 7.0 using 1N KOH, and the water was removed in vacuo leaving a solid. Chromatography of this solid on 80 ml of CHP-20P resin (Mitsubishi Chemical Industries) water and then 5% dimethylformamide in water gave 140 mg of (cis)-2-amino-1,9-dihydro-9-[3-(hydroxymethyl)cyclobutyl]-6H-purin-6-one as a solid having m.p. 275°–278° (dec.).

EXAMPLE 2

(cis)-3-(6-Amino-9H-purin-9-yl)cyclobutanemethanol

A. (cis)-3-(6-Amino-9H-purin-9-yl)cyclobutanemethanol, benzoate ester

To a solution of 720 mg (2.0 mmol) of 3[[(4-methylphenyl)sulfonyl]oxy]cyclobutanemethanol, benzoate ester (95% trans isomer and 5% cis isomer) in 20 ml of dry dimethylformamide under nitrogen was added adenine (405 mg, 3 mmol), 18-crown-6 (528 mg, 2 mmol), and potassium carbonate (414 mg, 3 mmol). The mixture was stirred at 110° for 18 hours and then concentrated in vacuo to a residue. Water was added and the suspension was adjusted to pH 7.0 using 1N hydrochloric acid. Removal of solvent in vacuo gave a residue, which was chromatographed over 200 ml of LPS-1 silica gel using 4% methanol in dichloromethane to give 430 mg of desired product as a white solid.

B. (cis)-3-(6-Amino-9H-purin-9-yl)-cyclobutanemethanol

To a solution of (cis)-3-(6-amino-9H-purin-9-yl)cyclobutanemethanol, benzoate ester (430 mg, 1.33 mmol) in dry methanol (20 ml) under nitrogen was added 88μl of 25% sodium methoxide in methanol. The mixture was stirred at 40° for 2 hours and then concentrated in vacuo to a residue, which was suspended in water (20 ml). The pH was adjusted to 7.0 using 1N hydrochloric acid, and the water was removed in vacuo leaving a residue. Chromatography of this residue on 200 ml of CHP-20P resin packed in water, using a gradient of 0–30% methanol in water, gave, after removal of solvents in vacuo, 205 mg of a hygroscopic solid. Lyophilization of this solid from water gave 167 mg of (cis)-3-(6-amino-9H-purin-9-yl)-cyclobutanemethanol as a hygroscopic, glassy solid having m.p. 85°–88°.

EXAMPLE 3

Treatment of Viral Infection in Cell Culture in Vitro

Assays were performed in cell culture systems to determine the concentrations of compounds that are effective in preventing several kinds of viral infections. The assays are described below, and the results are presented in Table 1.

Abbreviations:

HSV-1 (herpes simplex virus type 1, strain Schooler), HSV-2 (herpes simplex virus type 2, strain 186), VZV (varicella zoster virus, strain ELLEN), MuLV (murine leukemia virus, strain CAS), HIV (human immunodeficiency virus, strain HTLV-IIIB). Cell Culture Assays:

HSV-1, HSV-2, and VZV antiviral assays: Virus was adsorbed to WI-38 cell culture monolayers in 6 well culture plates (Costar, Cambridge, Mass.) for 1 hour prior to addition of maintenance medium containing duplicate dilutions of the test compound. Inhibition of plaque development was evaluated on fixed and stained monolayers after 4 days incubation at 37° C. for HSV-1 and HSV-2 and after 6-7 days incubation at 37° C. for VZV. $ID_{50}$ values were determined from the drug concentration which conferred at least a 50% plaque reduction compared to virus controls.

MuLV antiviral assay: Antiviral assays using MuLV were performed with some modification, as described by Rowe et al. and Shannon et al.. SC-1 cells were planted at approximately $2 \times 10^5$ cell per well in 6 well plates. After overnight incubation at 37° C., the cell cultures were sensitized with DEAE-Dextran for one hour at 37° C., rinsed and inoculated with MuLV. Cultures were re-fed with growth medium containing different concentrations of the test compound. After three more days at 37° C., cultures were re-fed with fresh medium plus test compounds and incubated at 37° C. for an additional 3 days. Cultures were then washed to remove medium, ultraviolet light irradiated, and planted with approximately $5 \times 10^5$ XC cells per well in cell growth medium containing the appropriate concentration of the test compound. The cultures were then incubated for an additional 4 days, with a re-feed using growth medium containing test compound at the second day following XC cell overlay. Finally the cultures were rinsed, stained and syncytial plaques were counted. References:

Rowe, W. P., Pugh, W. E., and Hartley, J. W., (1970), Plaque Assay Techniques for Murine Leukemia Viruses, Virology, 42: 1136–1139.

Shannon, W. M, Brockman, R. W., Westbrook L., Shaddix, S., and Shabel, F. M., (1974) Inhibition of Gross Leukemia Virus-Induced Plaque Formation in XC Cells by 3-Deazauridine, J. Natl., Cancer Inst., 52:199-205.

HIV antiviral assay: Suspensions of CEM cells (P. L. Nara, et. al., Nature 332, 469(1988)) were infected at a multiplicity of infection of 0.12 $TCID_{50}$/cell with HIV (strain HTLV-III B). After adsorption for 1-2 hours at 37° C., infected cells were diluted in growth medium (RPMI 1640 containing the antibiotics penicillin plus streptomycin and 10% fetal calf serum) to give a final cell concentration of $1 \times 10^4$ viable cells/culture well in the presence of serial dilutions of the test compound, starting at 100 μg/ml. Triplicate samples at each drug concentration were used. Cultures of uninfected CEM cells were similarly prepared and incubated with serial dilutions of test compound in duplicate. All assays were performed in 96 well disposable cell culture plates. Untreated (infected and uninfected) cells were included as controls. All cultures were incubated for 7 days at 37° C. in a humidified atmosphere containing 5% $CO_2$. Following incubation, viable cell numbers were counted in each well using a colorimetric assay following incubation of cells with XTT-PMS solution (XTT tetrazolium reagent plus phenazine methosulfate, PMS).

Percent reduction of viral cytopathic effect (CPE) in drug treated compared to untreated virus infected cells, and percent reduction of cell viability in drug treated uninfected cells compared to untreated controls were calculated and plotted versus the drug concentrations tested. From these plots, the $ID_{50}$ (the minimum drug concentration that inhibits CPE by 50%) for each drug was calculated. 2′, 3′-Dideoxycytidine was used as a positive drug control.

What is claimed is:
1. A compound having the formula

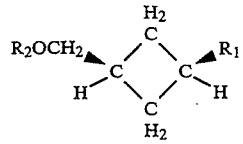

and its pharmaceutically acceptable salts wherein $R_1$ is

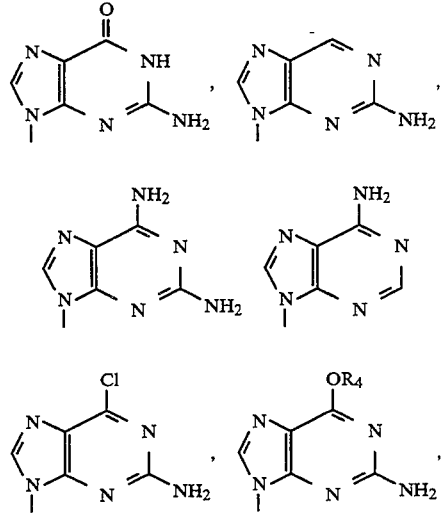

wherein $R_2$ is hydrogen, $-PO_3H_2$, or

TABLE 1

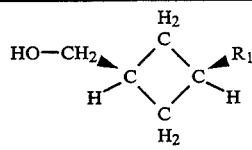

| $R_1$ | $ID_{50}(\mu M)$ for the following viruses | | | | |
|---|---|---|---|---|---|
| | HSV-1 | HSV-2 | VZV | MuLV | HIV |
| (structure 1) | 9-21 | 9-21 | 21 | 43-106 | 230*** |
| (structure 2) | 456* | 456* | >114** | 23-46 | 301**** |

*Cytotoxic at 456 μM by microscopic examination of the cell sheet.
**Cytotoxic at 228 μM by microscopic examination of the cell sheet.
***Minimum cytotoxic drug concentration that reduces cell viability by 50% is >425 μM.
****Minimum cytotoxic drug concentration that reduces cell viability by 50% is >456 μM.

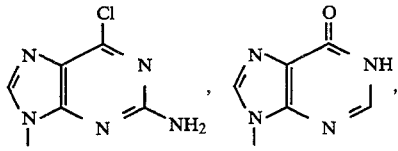

wherein R$_3$ is hydrogen, alkyl, substituted alkyl, or aryl, and R$_4$ is alkyl wherein the term alkyl refers to both straight and branched chain groups having one to ten carbon atoms; the term substituted alkyl refers to alkyl groups having one or more substituents wherein the substituent is halogen, amino, azido, hydroxy, cyano, trialkylammonium (wherein each alkyl group has 1 to 6 carbons), alkoxy of 1 to 6 carbons, aryl and carboxy; the term aryl refers to phenyl and phenyl substituted with one, two or three substituents wherein the substituent is alkyl of 1 to 6 carbons, alkoxy of 1 to 6 carbons, halogen, trifluoromethyl, amino, alkylamino, dialkylamino, nitro, cyano, alkanoyloxy of 2 to 11 carbons, carboxy, carbamoyl and hydroxy.

2. A compound in accordance with claim 1 wherein R$_2$ is hydrogen.

3. A compound according to claim 1 wherein R$_1$ is

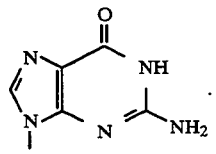

4. A compound according to claim 1 wherein R$_1$ is

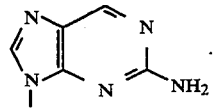

5. A compound according to claim 1 wherein R$_1$ is

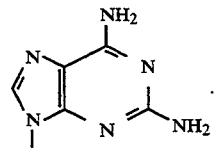

6. A compound according to claim 1 wherein R$_1$ is

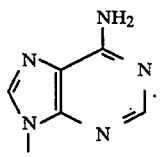

7. A compound according to claim 1, (cis)-2-amino-1,9-dihydro-9-[3-(hydroxymethyl)cyclobutyl]-6H-purin-6-one.

8. A compound according to claim 1, (cis)-3-(6-Amino-9H-purin-9-yl)cyclobutanemethanol.

9. A compound according to claim 1 wherein R$_1$ is

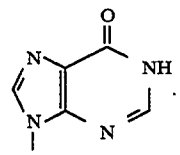

10. A compound according to claim 1 wherein R$_1$ is

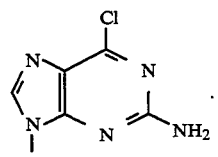

11. A compound according to claim 1 wherein R$_1$ is

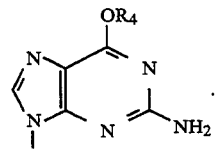

12. A compound according to claim 1 wherein R$_1$ is

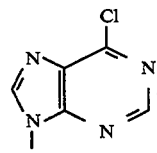

* * * * *